(12) United States Patent
Israelsson et al.

(10) Patent No.: US 11,169,143 B2
(45) Date of Patent: **\*Nov. 9, 2021**

(54) SYSTEM AND METHOD FOR CONTROLLING A FLOW THROUGH A PNEUMATIC SYSTEM

(71) Applicant: Shenzhen Mindray Bio-Medical Electronics Co., Ltd., Shenzhen (CN)

(72) Inventors: Sigun Israelsson, Jarfalla (SE); Peter Svedmyr, Bromma (SE); Johan Werner, Skogas (SE); Anders Finn, Vittinge (SE); Mathias Eklund, Stockholm (SE); Torbjörn Boxell, Älvsjö (SE)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/854,113

(22) Filed: Apr. 21, 2020

(65) Prior Publication Data
US 2020/0326328 A1 Oct. 15, 2020

Related U.S. Application Data

(63) Continuation of application No. 14/939,957, filed on Nov. 12, 2015, now Pat. No. 10,627,391.

(30) Foreign Application Priority Data

Nov. 13, 2014 (EP) ..................... 14192931

(51) Int. Cl.
*G01N 33/497* (2006.01)
*A61B 5/08* (2006.01)
(Continued)

(52) U.S. Cl.
CPC .......... *G01N 33/497* (2013.01); *A61B 5/082* (2013.01); *A61M 16/0069* (2014.02);
(Continued)

(58) Field of Classification Search
CPC ............ G01N 33/497; A61M 16/0069; A61M 2205/42; A61M 16/0666;
(Continued)

(56) References Cited

U.S. PATENT DOCUMENTS 6,024,924 A 2/2000 Schoning et al.
6,067,983 A 5/2000 Stenzler
(Continued)

*Primary Examiner* — Peter J Macchiarolo
*Assistant Examiner* — Anthony W Megna Fuentes
(74) *Attorney, Agent, or Firm* — Kory D. Christensen

(57) ABSTRACT

A device, system and method related to a pneumatic system for fluid analysis. The device, system and method comprises a connection interface for a fluid analyser unit, a connection interface for a pump unit, a flow sensor and a pressure sensor. The device, system and method further comprises a control unit for calculating a pump stroke force or amplitude, and/or pump frequency based on measurements from the flow sensor and the pressure sensor for obtaining a constant flow through the pneumatic system.

11 Claims, 4 Drawing Sheets

(51) Int. Cl.
  *A61M 16/10*  (2006.01)
  *A61M 16/00*  (2006.01)
  *A61M 16/06*  (2006.01)
  *A61M 16/01*  (2006.01)
  *A61M 16/08*  (2006.01)

(52) U.S. Cl.
  CPC ......... *A61M 16/01* (2013.01); *A61M 16/0666* (2013.01); *A61M 16/085* (2014.02); *A61M 2016/003* (2013.01); *A61M 2016/0027* (2013.01); *A61M 2016/1025* (2013.01); *A61M 2205/3358* (2013.01); *A61M 2205/42* (2013.01); *A61M 2205/50* (2013.01)

(58) Field of Classification Search
  CPC .. A61M 2016/0027; A61M 2016/1025; A61M 2205/50; A61M 2016/003; A61M 2205/3358; A61M 16/01; A61M 16/085; A61M 16/0045; A61M 16/0057; A61B 5/082

See application file for complete search history.

(56) References Cited

U.S. PATENT DOCUMENTS

| | | | |
|---|---|---|---|
| 10,627,391 B2* | 4/2020 | Israelsson | A61M 16/0069 |
| 2003/0044993 A1 | 3/2003 | Yatscoff et al. | |
| 2004/0186391 A1 | 9/2004 | Pierry et al. | |
| 2005/0103346 A1 | 5/2005 | Noble | |
| 2006/0201499 A1 | 9/2006 | Muellinger et al. | |
| 2009/0056409 A1 | 3/2009 | Howard et al. | |
| 2009/0118633 A1 | 5/2009 | Jaffe et al. | |
| 2010/0163023 A1 | 7/2010 | Singh | |
| 2015/0025407 A1 | 1/2015 | Eichler et al. | |

\* cited by examiner

SYSTEM AND METHOD FOR CONTROLLING A FLOW THROUGH A PNEUMATIC SYSTEM

CROSS-REFERENCE TO RELATED APPLICATIONS

This application is a continuation of U.S. patent application Ser. No. 14/939,957, filed Nov. 12, 2015, for SYSTEM AND METHOD FOR CONTROLLING A FLOW THROUGH A PNEUMATIC SYSTEM, now U.S. Pat. No. 10,627,391, issued Apr. 21, 2020, which claims the benefit of European Patent Application No. 14192931.5, filed Nov. 13, 2014, each of which is incorporated herein by reference.

BACKGROUND OF THE INVENTION

Field of the Invention

This disclosure pertains in general to a pneumatic system, such as a pneumatic manifold. More particularly the disclosure relates to a pneumatic system for a fluid analyser and for controlling the flow through a pneumatic system. In particular this relates to pneumatic systems for fluid analysers used in, for example, mechanical ventilators, anaesthesia machines, or patient monitoring to detect a composition of expiration and/or inspiration fluids.

Description of the Prior Art

In standard pneumatic systems on the market, different components of the system, such as valves, pumps, flow and pressure sensors, and measuring cells are fluidly connected by metal or plastic tubes and connectors. These simple systems are associated with a number of drawbacks, for example, that the many connection points between tubing and connected components increases the risks of leakage in the system. The large number of components makes the systems very complex to assembly, which adds cost and increases the risk of assembly operator caused errors.

Also, dead space and dimensions changes in the fluid path caused by the many connections leads to an unwanted increased system delay, rise and fall times.

There are some high-end systems that utilize an integrated design approach. These systems use a manifold instead of tubes to distribute at least part of the fluid to the different components of the device. The existing high-end systems still have some drawbacks, for example, external buffer volumes may be used outside the manifold to try to obtain a ripple free fluid flow. Rise and delay times may be too high. Also, the current integrated designs may not be able to provide fast and accurate, control and regulation of the system.

A side-stream gas analyzer is connected to the patient breathing circuit, taking a small portion sampling flow from the breathing circuit used as gas sample for the analysis. There are two common diaphragm pump techniques used in gas analyzing devices to create the sampling flow, a piston pump and a voice coil pump. A piston pump transfers a defined volume of fluid from one point to another by a piston action created by a rotating motor. The pump volume is fixed but the pump frequency can be varied to obtain a desired flow.

A voice coil pump transfers a defined volume of fluid by the act of a voice coil. This technique can vary the pump volume by change of stroke amplitude and stroke frequency to get a desired flow.

A problem that occurs in dynamic gas measurement in mechanically ventilated patients is that the pressure in the patient circuit varies within a breath with pressure peaks at the end of the inspiration phase. For spontaneous breathing patients the situation is opposite with pressure peaks in the expiration phase. An increased pressure compresses the gas which results in a larger portion of volume being transferred under higher pressure if the pressure is not compensated for.

Prior art in the field of side-stream analyzers tries to keep constant flow over an averaged time period of several breaths and do not regulate on pressure changes within a breath. When not doing regulation during a breath cycle, the drawn sample flow is varying several percentages with the pressure. But more and more host devices and advanced clinical parameter calculations requires a better flow control than prior art.

Hence, an improved integrated design would be advantageous, and in particular an integrated design that decreases the ripples, improves the rise, fall, and delay times to provide for an improved control and regulation of the system. Preferably the integrated design should be easy to produce and service, and be more energy efficient than the current systems.

SUMMARY OF THE DISCLOSURE

Accordingly, embodiments of the present disclosure preferably seek to mitigate, alleviate or eliminate one or more deficiencies, disadvantages or issues in the art, such as the above-identified, singly or in any combination by providing a device, system or method according to the appended patent claims for providing an improved pneumatic system, such as a pneumatic manifold, for a gas analyser and regulation of the pump to compensate for dynamic pressure variations. These pneumatic manifolds may be used, for example, in fluid analysers used in, for example, mechanical ventilators, anaesthesia machines, or patient monitoring to detect composition of expiration and/or inspiration fluids. The improvements to the pneumatic system make it possible to improve rise-time performance, cancel ripple without external volumes and perform dynamic pressure regulation and control the flow during a breath cycle when detecting a composition of expiration and/or inspiration fluids.

In an aspect of the invention a pneumatic system for fluid analysis of expiratory and/or inspiratory breath is disclosed. The pneumatic system comprises a connection interface for a fluid analyser unit, a connection interface for a pump unit, a flow sensor and/or a pressure sensor, and a control unit for calculating a pump stroke force and/or pump frequency based on measurements from the flow sensor and/or the pressure sensor for obtaining a constant flow through the pneumatic system during a breath cycle with dynamic pressure, such as an inhale and/or an exhale.

By regulating the pump as disclosed herein, the flow can be adjusted for the dynamic pressure during a single breath making it possible to obtain a constant flow during a single inhale or exhale. Hence the system will compensate for a patients breathing pattern on a breath to breath level.

In some examples, the pneumatic system may have a buffer volume arranged between the connection interface and the connection interface for a pump unit.

The buffer volume is used to cancel ripple, improve pump performance, and to improve flow regulation.

In some further examples of the disclosure, the pneumatic system comprises a pneumatic manifold.

As disclosed herein, the use of a manifold will further optimize the performance of the pneumatic system and improve the pump regulation.

In a further aspect of the disclosure, a fluid analysing system is disclosed. The system comprises a pneumatic system as disclosed herein, a pump unit connected to the connection interface for a pump unit, and a fluid analyser unit connected to the connection interface for a fluid analyser unit. The control unit is configured to regulate a pump stroke force and/or pump frequency of the pump unit based on measurements from the flow sensor and the absolute pressure sensor for obtaining a constant flow through the pneumatic system during a breath cycle with dynamic pressure, such as an inhale and/or an exhale.

In another aspect of the disclosure, a method of dynamic pressure regulation of a pump-flow is disclosed. The method comprising measuring a flow and/or a pressure of a fluid through the pneumatic system, and calculating a pump stroke force and/or pump frequency based on the measurements for obtaining a constant flow through the pneumatic system during a breath cycle with dynamic pressure, such as an inhale and/or an exhale.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of embodiments of the present disclosure, reference being made to the accompanying drawings, in which.

DESCRIPTION OF EMBODIMENTS

Specific examples of the disclosure will now be described with reference to the accompanying drawings. This disclosure may, however, be embodied in many different forms and should not be construed as limited to the examples set forth herein; rather, these examples are provided so that this disclosure will be thorough and complete, and will fully convey the scope of the disclosure to those skilled in the art. The scope of the disclosure is only limited by the appended patent claims.

Figure 1:
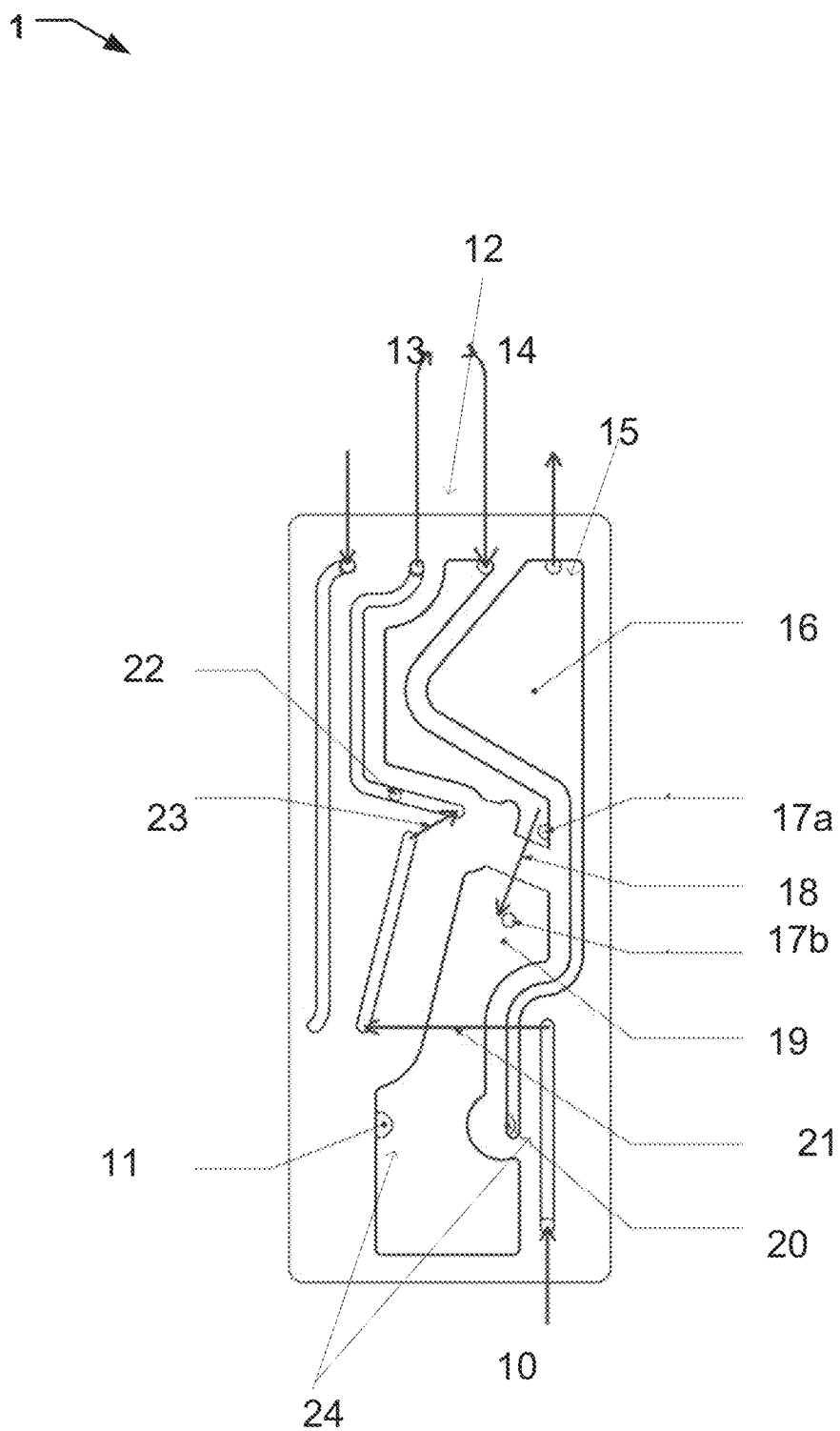
FIG. 1 illustrates a flow path of an exemplary pneumatic manifold for fluid analysis.

FIG. 1 illustrates a flow path of an exemplary pneumatic manifold 1 for fluid analysis. The fluid may for example be a sample of expiratory gas or inspiration gas from a subject, such as a patient connected to a mechanical ventilator, an anaesthesia machine, or a patient monitoring device. A pneumatic manifold is used to minimize the number of tubes and connectors etc. which is normally used in a pneumatic system. By decreasing the number of tubes and connectors, the pneumatic system may be cheaper to manufacture. The used pneumatic manifold may keep the wave-front intact with minimum distortion as it has not only fewer tubes and connectors but also utilizes straight channels without any dimension transitions and having connection point with no or little dead-space connection; hence the system may have an improved rise- and fall time and delay time. Improved rise and fall times are important when detecting fast changes in the breathing gas compound, the signal wavefront needs to be kept with minimal distortion when passing through a pneumatic system. Fast transitions in an increase of a concentration and in a decrease of a concentration are critical for correct gas compound analysis.

The pneumatic manifold will at the same time be faster and be more robust. The likelihood of leakage is reduced compared to a traditionally pneumatic system due to less connection points.

A pneumatic manifold may be made, for example, from two parts, a top element and a bottom element which are fastened together by either welding, or soldering, e.g. by ultrasound welding. Alternatively, the two elements may be fastened by an adhesive. As a further alternative, the two parts may be releasably attached using means such as screws or other means known to the person skilled in the art.

Alternatively, the manifold may be made, for example, of three or more parts, such as one bottom element and two top elements. As a further alternative, the pneumatic manifold may be molded as a single unit, such as by utilizing 3D printing.

In one example, the, in FIG. 1, illustrated pneumatic manifold includes a connection interface for a fluid analyser unit 12. The fluid analyser unit has an inlet 14 and an outlet 13. The pneumatic manifold can also include another connection interface for a fluid analyser unit 23. The connection interface for a fluid analyser unit includes an inlet 14 for passing a fluid into the manifold from the fluid analyser unit. The fluid analyser unit may be an analyser unit. Most fluid analysers are sensitive to pneumatic ripples as well as rise, fall and delay times of the system.

Example of analyser units are Oxygen sensors for measuring the concentration of Oxygen in a fluid, measuring cuvettes for spectroscopic measurements or other forms of analysers such as ultra-sound analysers or colorimetric.

The pneumatic manifold further includes a connection interface for a pump unit 24. The connection interface for a pump unit has an inlet 20 and an outlet 11. The pump is used for pumping the fluid around the system. A restrictor 18 may be arranged in a flow path between the connection interface for a pump unit and the connection interface for a fluid analyser unit. For example, the flow path may be from an inlet 14 of the connection interface of a fluid analyser unit 12 to an outlet of the connection interface of a pump unit 11. A buffer volume 19 is arranged between the connection interface for a pump unit and the restrictor. If the system does not require a restrictor the buffer volume may be arranged in a flow path between the connection interface for a pump unit and the connection interface for a fluid analyser unit. For example, the flow path may be from an inlet of the connection interface of a fluid analyser unit to an outlet of the connection interface of a pump unit.

The buffer volume may act as a constant flow control cavity, a pump capacity improving cavity and as a ripple cancellation cavity, all parameters that otherwise may impact the measurement system. By arranging the buffer volume after the fluid analyser and between the restrictor and the pump, the pneumatic ripple may be decreased. The pneumatic ripple is caused by the pump pumping the fluid and vibrations from the pump itself. As the pneumatic ripple may have a negative effect on the measurements done by the fluid analyser, such as an oxygen sensor or a measuring cuvette for spectroscopic measurements, a decrease in the pneumatic ripple may thereby increase the measurement performance as the flow may be more constant through the fluid analyser unit and over the restrictor.

The capacity of the pump may also be optimized by this arrangement of the buffer volume since the pump is working under more favourable conditions as low under pressure conditions may be avoided which leads to full stroke force. The buffer volume may act as a capacitor making it possible for the pump to avoid demanding under pressure situation. This arrangement enables the pump to work with full stroke length giving full capacity. This may also have an effect on the energy efficiency of the pump, as an optimized flow may lead to an improved energy consumption of the pump as the pump may work at an increased stroke length and at a decreased stroke frequency and still provide a more even flow over the restrictor and through any fluid analysers.

As disclosed above, the buffer volume between restrictor and pump must be carefully optimized to obtain high end performance of the system. The three main parameters to optimize for are pneumatic ripple cancelation, pump performance, and flow regulation.

The buffer volume must be large enough to cancel out any pneumatic ripple. Pneumatic ripple affects measurements in, for example, a cuvette for spectroscopic measurements and O2 sensor as well as the ability to measure a flow via pressure drop over the restrictor.

The lower limit of the size of the buffer volume may foremost depend on pump type, pump frequency, pump stroke volume, pump max capacity and restrictor size. In this aspect there is no upper limit to the size of the buffer volume.

On the other hand the volume must be large enough to enable the pump to work efficiently. If the available volume is too small, a large under pressure is created which affects the pumps performance negatively.

The lower limit of the size of the volume will foremost depend on pump type, pump frequency, pump stroke volume, pump max capacity and restrictor size. When only considering this aspect, there is no upper limit to the size of the volume.

The buffer volume must also be small enough for the system to quickly react to changes made in pump stroke length aiming to regulate the flow. If the volume is too large the flow regulation will be slow and inaccurate. In this aspect there is no lower limit to the size of the volume but the upper limit of the size of the volume will foremost depend on pump type, pump frequency, pump stroke volume, pump max capacity and restrictor size in relation to the pressure situation of the pumped fluid sample.

Alternatively, in some examples, the restrictor may be arranged after the pump interface. The restrictor may then still be used for measuring, for example, a differential pressure or a flow. If the restrictor is arranged after the pump, the measured data may include ripples which would have been canceled by the buffer volume arranged before the pump and which have to be compensated for.

Figure 2A:
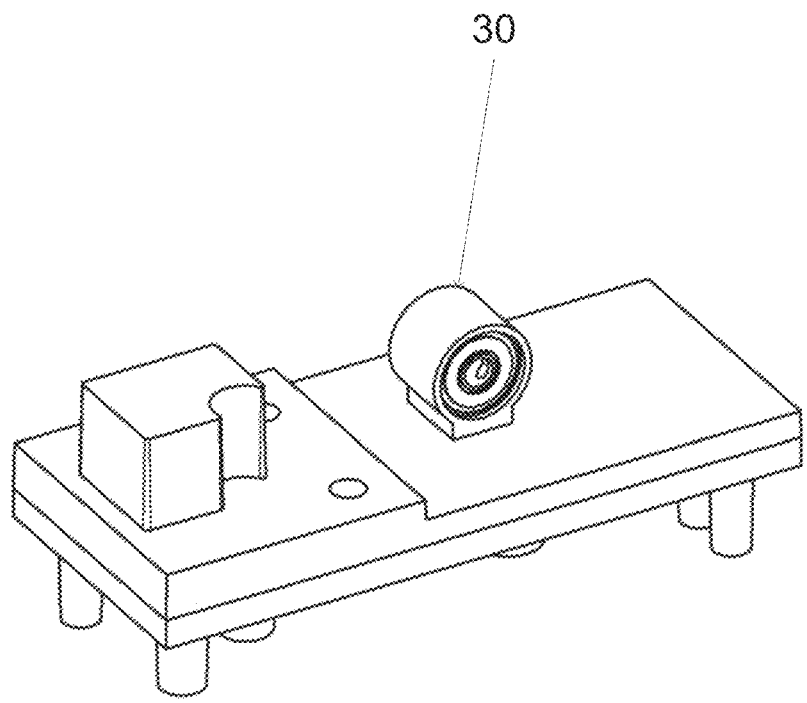
FIGS. 2A and 2B are illustrating an exemplary pneumatic manifold with an integrated cuvette.
Figure 2B:
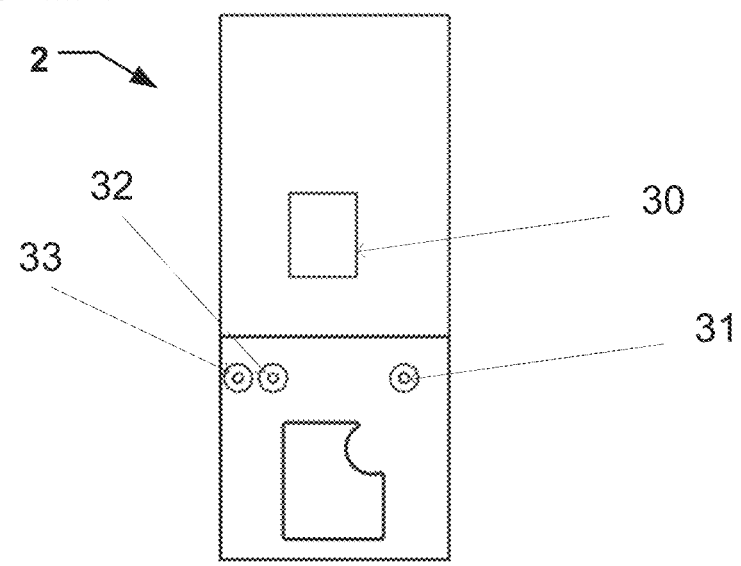
Figure 3:
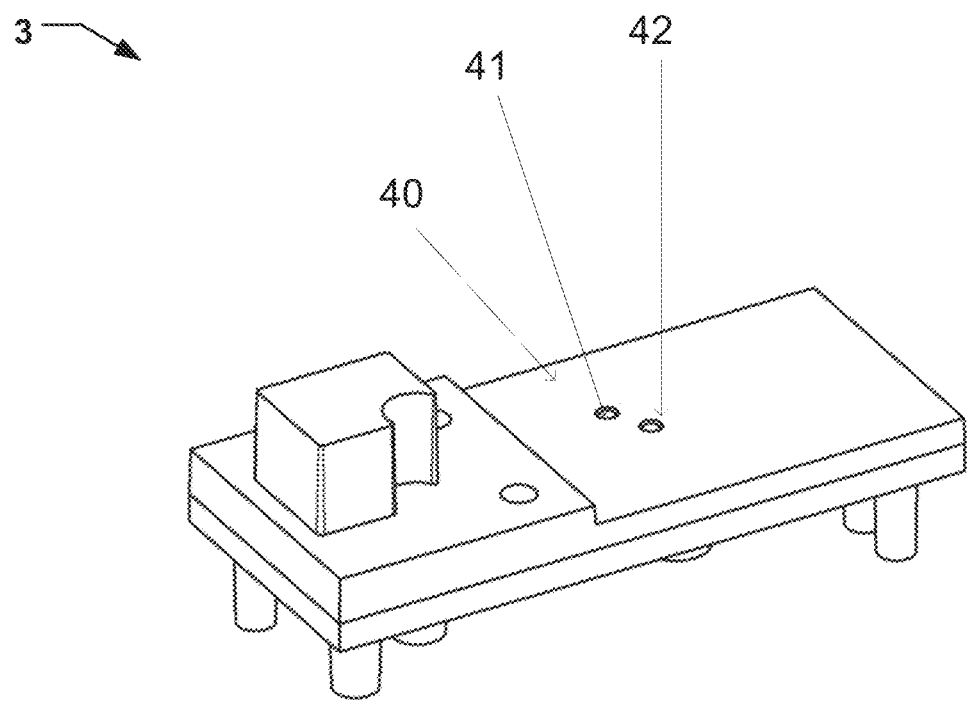
FIG. 3 is illustrating an exemplary pneumatic manifold without a cuvette attached.

Additionally and/or alternatively, in some examples of a pneumatic manifold the fluid analyser unit 30 may be a cuvette arranged either directly onto the pneumatic manifold or as an integrated part of the manifold. One such example of a pneumatic manifold with integrated cuvette is illustrated in FIGS. 2A and 2B. FIG. 3 illustrates an example of a manifold 40 with a connector to a cuvette having an outlet 41 to the cuvette and an inlet 42 from the cuvette.

The cuvette may be used for electromagnetic radiation measurements, such as spectroscopic measurements using infrared radiation and/or visible light and/or ultraviolent light.

When the cuvette is an attachable member, the pneumatic manifold has a connection interface with an inlet and an outlet for connecting the cuvette to the pneumatic manifold.

The inlet to the cuvette may be fluidically connected to an inlet of the pneumatic manifold for a sample of fluid, such as an expiratory or inspiratory fluid from a subject. The outlet from the cuvette may be fluidically connected to the outlet of the connection interface for a pump unit.

Additionally, in some examples, the pneumatic manifold may have two or more fluid analyser units, such as a cuvette and a O2 sensor. Then the cuvette may be arranged between an inlet of the pneumatic manifold for a sample of fluid and the outlet of the connection interface for a fluid analyser unit. They may also be arranged the other way around.

By arranging the cuvette before the second fluid analyser unit (e.g. a O2 sensor), the rise, fall, and delay times may not be effected by the second fluid analyser unit before the fluid is analysed by the measurement system associated to the cuvette.

The advantages of arranging the cuvette to the pneumatic manifold or as an integrated part of the pneumatic manifold, for example, as illustrated in FIG. 2A, is that the rise, fall, and delay times may be improved. The improvement of the rise-time comes from the smaller flow volumes and the short and straight channels without any dimension transitions before the cuvette, smaller dead-space connection points, which is made possible by the use of a pneumatic manifold. Also, the positioning and improved interface between the cuvette and the pneumatic manifold reduces the number of tubes and tube connectors needed which further improves the rise-time. All pneumatic connections may contribute to increasing the rise-time as the wave-front may be distorted.

By having the cuvette integrated into the manifold the rise-time may be even more improved, compared to a cuvette connected by an interface, as there is no coupling needed between the cuvette and the pneumatic manifold.

Additionally, the pneumatic manifold may have a valve that may be used to couple reference air, such as ambient air from the room into the pneumatic manifold via a reference inlet. The reference air could be used as a reference to check if the analysing system is working properly and compensates for air.

Additionally, in some examples, the pump which is connectable to the pneumatic manifold may pump the fluid back into the pneumatic manifold via an inlet in the connection interface for a pump unit. The fluid is then pumped to an outlet 15 of the pneumatic manifold which may be either connected to an evacuation system at a hospital or re-circulated to the patient. For some types of measurements, such as CO2, the exhaust may be sent direct to ambient.

In some examples of the pneumatic manifold, the restrictor may be used to obtain a pressure drop and then use differential pressure sensors 17a, 17b across the flow restrictor. The differential pressure sensors 17a, 17b may be used as a flow sensor for measuring the flow. Other ways of measuring flow are e.g. mass flow meters or thermal flow meters.

The restrictor may also provide, in combination with the flow channels of the pneumatic system, a pressure drop from the high pressure on the patients side compared the low atmosphere pressure on the EVAC side. The pressure drop of the restrictor counteracts the through flow caused by the pressure difference between inlet and outlet.

Additionally and/or alternatively a barometric pressure sensor 22 may be also be arranged in a channel of the manifold to measure the barometric pressure. The barometric pressure may be used as an in-parameter in the calculation of the concentration of a substance or compound in the fluid to compensate for pressure variations. The barometric pressure may also be used as parameter for pump regulation to maintain a constant flow during a breath cycle, such as during an inhale and/or an exhale. For example, when the pressure goes up the pump force required to maintain the flow will go down and vice versa.

In one example, as the one illustrated in FIG. 2A, the barometric pressure condition is measured in the cuvette and used to compensate the spectroscopic measurement for pressure variations. The same measured barometric pressure condition may be used for pump regulation. If no cuvette is used the barometric pressure may be measured at any place between the inlet to the pneumatic system and the outlet for the pump.

Alternatives to measuring the barometric pressure for pump regulation may be, a Gauge pressure sensor which measures the pressure in relation to atmosphere, an absolute measure sensor, a Differential pressure sensor measuring the pressure in relation to a point in the system having constant pressure.

Additionally and or alternatively, in some examples the system has a flow sensor. The barometric pressure condition may then be measured at the flow sensor to compensate the flow measurement for pressure variations, as well as enabling a fast regulation of the pump to a true constant flow.

As an alternative to measuring the barometric pressure condition at the flow sensor, the barometric pressure condition may be measured at another location before the pump, such as at the cuvette as illustrated in FIG. 1. The measured barometric pressure condition may then still be used compensate the flow measurement for the pressure variations. The drawback is that there may be an offset error compared to when measuring the barometric pressure conditions at the flow sensor but this could be handled using, for example, a calibration routine.

Additionally, temperature compensation of the flow in current operation condition can also be made through a thermistor sensor placed near the flow sensor.

Additionally, due to the improved handling of pneumatic ripples and the improved pump capacity of the herein above described pneumatic manifold, it is possible to perform dynamic pressure regulation during a breath cycle, such as during an exhale and/or an inhale. A pump regulation algorithm works to keep the flow constant through the analyzing system. The algorithm is a method of controlling a constant flow over varying dynamic pressure conditions during a breath cycle, such as during an inhale and/or an exhale, by utilizes a control loop feedback controller over the measured momentary flow.

The control unit has an improved control method implemented, introducing feed-forward control through information of the barometric pressure.

This speeds up the regulation substantially and enables the control unit to follow the fast dynamic pressure conditions within a breath cycle.

In the method above the pump regulation is based on the measured barometric pressure. By also using the differential pressure or flow measurements from the restrictor as in-parameters to a control unit the regulation may be further improved.

The feed-forward control through the barometric pressure makes it possible for the control loop to adjust on a smaller flow error and regulate faster Alternatively, the pump regulation may be done using only data from the flow sensor as an in-parameter. In this case, to compensate for the varying pressure situations a momentary barometric pressure over the flow sensor on the patient circuit side may be measured as well. This is done by measuring the barometric pressure of the flow in the pneumatic manifold, instant and with fast response.

The control unit calculates an optimal pump stroke force and/or pump frequency based on the measured pressures and/or fluid flow. The optimal pump stroke force and/or pump frequency are then fed into the pump control. Depending on the pump used, the pump stroke amplitude may be the parameter to regulate instead of the pump stroke force.

Alternatively, the control unit may calculate optimized pump stroke force for a defined pump frequency which then is fed into the pump control. As a further alternative, the control unit may calculate an optimal pump frequency for a defined stroke force which then is fed into the pump control. The output force and/or frequency may constantly be adjusted to generate an optimal pump flow adjusted for pressure variations between each breath of a patient. Additionally, in some examples of the regulation, the output force and/or frequency may also be constantly adjusted to generate an optimal pump flow adjusted for pressure variations in each breath.

By using a voice coil based pump instead of a piston based pump, the pump regulation to achieve a constant pump flow may be made almost noise-free as changing stroke forces of a voice coil may be made almost noise-free compared to the acoustic noise caused by a piston pump when changing pump frequencies. The acoustic noise may be perceived as very disturbing for patients.

With a fast update rate on the flow and/or pressure measurements, the pump may regulate its stroke volume fast within a breath cycle, such as during an inhale and/or an exhale. The only delays in adjusting the stroke volume to the momentary pressure situation is how fast the pump may change its membrane position and possible volumes in the system between the restrictor and the pump which may act as capacitors, introducing delays in the dynamic pressure regulation. Minimized volume between restrictor and pump is therefore preferred. When minimizing the volume between the flow restrictor and the pump, the flow restrictor may restrict the flow which passes through and within a pump stroke, the gas between the restrictor and the pump may be compressed and decompressed. The pressure equalization is constrained caused by the flow restriction. It is an accordion effect that limits the pump from reaching full capacity and causes ripples. Hence the volume has to be large enough for handling these effects.

These two constrains for fast regulation relates to the mechanical design of the measurement system. In this case the integrated pneumatic manifold. When providing a gas analyzer with dynamic pressure regulation during an exhale or an inhale, higher demand on the pneumatic manifold design is required. An optimized volume in between the restrictor and the pump is required as described herein above in relation to the buffer volume.

Additionally, by reducing the pneumatic ripple the system noise originating from the ripple may also be reduced. The noise from the pneumatic ripple may sometimes be a nuisance for the subject connected to a mechanical ventilator, an anaesthesia machine, or a patient monitoring device. In some further examples as seen in FIG. 1, the pneumatic manifold may include a silencer 16 to further reduce the noise from the pneumatic ripple as the noise may be a nuisance for a subject connected to a mechanical ventilator, an anaesthesia machine, or a patient monitoring device. In the illustration the silencer is positioned at the gas evacuation outlet 15 but further silencers may be used at other positions in the pneumatic system. Two techniques may be used to reduce acoustic noise in a pneumatic manifold. A resistance silencer which utilizes resonant cavities and sudden section changes to break up pressure waves in the flow caused by, for example pump strokes.

Additionally and/or alternatively, a dissipative silencer may be used which utilizes sound wave absorbing material. In some examples of a silencer, a combination of both techniques is used to reduce both high and low frequency noise.

As such, the fluid flow, as illustrated in exemplary FIG. 1, begins with the fluid entering the pneumatic manifold 1 through an inlet 10. The fluid may then flow across a valve 21. The fluid may flow through a connection interface for fluid analyser unit 23 and through a fluid analyser unit (which is not shown in FIG. 1 but is represented by a dotted box). A barometric pressure sensor 22 can sense the pressure of the fluid. Then the fluid may pass through another connection interface for fluid analyser unit 12 by flowing out of the pneumatic manifold 1 through outlet 13, through a fluid analyser unit (which is not shown in FIG. 1 but is represented by a dotted box), and back into the pneumatic manifold 1 through inlet 14. In at least one example, there may be one fluid analyser unit. In other examples, there may be more than one fluid analyser unit, for example as illustrated in FIG. 1. The fluid, as in FIG. 1, then can flow through a restrictor 18 into a buffer volume 19. The fluid then can pass through a connection interface for a pump unit 24 which includes an outlet 11 to a pump unit 25 and an inlet 20 from a pump unit 25. The pump unit 25 is not shown in FIG. 1 but is represented by a dotted box. The fluid can then flow through a silencer 16 and out of the pneumatic manifold 1 through an outlet 15.

Figure 4:
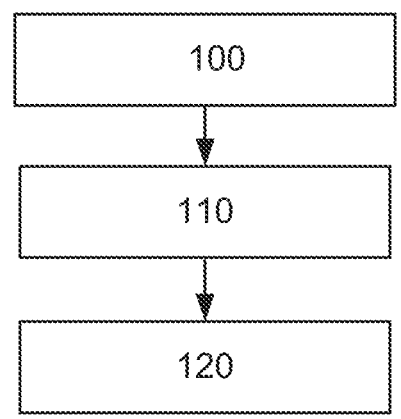
FIG. 4 is illustrating a flow-chart over an exemplary method of regulating a pump.

FIG. 4 is illustrating a flow-chart 4 over an exemplary method of dynamic pressure regulation of a pump-flow during a breath cycle, such as during an exhale and/or an inhale. The method comprises, an optional step of, arranging 100 a buffer volume in a pneumatic system between a connection interface for a pump unit and a connection interface for a fluid analyser unit. The method further comprises measuring 110 a flow and a barometric pressure of a fluid through the pneumatic system and calculating 120 a pump stroke force and/or pump frequency based on the measurements for obtaining a constant flow through a pneumatic system during a breath cycle with dynamic pressure, such as an inhale and/or an exhale.

By arranging 100 the buffer volume, which may act as a constant flow control cavity, a pump capacity improving cavity, and as a ripple cancellation cavity, an improvement in the measurement of all parameters that otherwise may impact the measurement system will be achieved.

While several examples of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Also, different method steps than those described above, performing the method by hardware, may be provided within the scope of the disclosure. The different features and steps of the disclosure may be combined in other combinations than those described. The scope of the invention is only limited by the appended patent claims.

The invention claimed is:

1. A pneumatic system for fluid analysis of expiratory and/or inspiratory breath, comprising:
    a connection interface for a fluid analyzer;
    a connection interface for a pump;
    a buffer volume arranged between said connection interface for the fluid analyzer and said connection interface for the pump, the buffer volume defining a volumetric space configured to enable the pump to operate at a full stroke length and to cancel out pneumatic ripple in the pneumatic system;
    a flow sensor and/or a pressure sensor; and
    a controller configured to calculate a pump stroke force and/or pump frequency based on measurements from said flow sensor and/or said pressure sensor for obtaining a constant flow through said pneumatic system during a breath cycle with dynamic pressure.

2. The pneumatic system according to claim 1, wherein said connection interface for the fluid analyzer is configured to send the fluid to and receive a fluid from a cuvette, and wherein said cuvette is configured for electromagnetic radiation measurements.

3. The pneumatic system according to claim 2, further comprising a pneumatic manifold including said connection interface of the pump and said connection interface of the fluid analyzer, wherein said connection interface for the fluid analyzer is configured to send a fluid to and receive the fluid from a cuvette, wherein said cuvette is an integrated part of a flow path of said pneumatic manifold.

4. The pneumatic system according to claim 2, to wherein said fluid analyzer is an oxygen sensor.

5. The pneumatic system according to claim 2, wherein a restrictor is arranged between said connection interface for the fluid analyzer and said buffer volume; and wherein said restrictor has a measuring element configured to measure a flow over said restrictor.

6. The pneumatic system according to claim 2, wherein said connection interface for the fluid analyzer comprises an inlet and an outlet for passing the fluid to and from said fluid analyzer.

7. The pneumatic system according to claim 6, wherein a flow path between said connection interface for the pump and said connection interface for the fluid analyzer is fluidically connected to said inlet of said connection interface for the fluid analyzer and to said outlet of said connection interface for the pump.

8. A fluid analyzing system comprising:
    a pneumatic system for fluid analysis according to claim 1;
    a pump connected to said connection interface for the pump; and
    a fluid analyzer connected to said connection interface for the fluid analyzer;
    wherein said controller is configured to regulate a pump stroke force and/or pump frequency of said pump based on measurements from said flow sensor and/or said pressure sensor for obtaining a constant flow through said pneumatic system during the breath cycle with dynamic pressure.

9. The system according to claim 8, wherein said pump is configured to pump the fluid from said fluid analyzer, through a restrictor, and into the buffer volume before said fluid is pumped out of said pneumatic manifold by said pump.

10. The system according to claim 8, wherein said pneumatic system comprises at least two fluid analyzers, wherein one is a cuvette configured for electromagnetic radiation measurements arranged in fluid connection to an inlet into said pneumatic system and an outlet of a connection interface for a second fluid analyzer; so that the fluid to be analyzed passes from said inlet into the cuvette and further into said second fluid analyzer via said outlet of said connection interface for the second fluid analyzer.

11. The system according to claim 8, wherein said pneumatic system further comprises a valve arranged to select between the fluid to be analyzed or a reference fluid from a reference inlet.

* * * * *